(12) United States Patent
Adimurthy et al.

(10) Patent No.: US 8,957,239 B2
(45) Date of Patent: Feb. 17, 2015

(54) PROCESS FOR THE ECO-FRIENDLY PREPARATION OF 3, 5-DIBROMO-4-HYDROXYBENZONITRILE

(75) Inventors: Subbarayappa Adimurthy, Bhavnagar (IN); Gadde Ramachandraiah, Bhavnagar (IN); Girdhar Joshi, Bhavnagar (IN); Rajendra Patil, Bhavnagar (IN); Maheshkumar Ramniklal Gandhi, Bhavnagar (IN); Mallampati Subbareddy, Bhavnagar (IN); Pratyush Maiti, Bhavnagar (IN)

(73) Assignee: Council of Scientific and Industrial Research, New Delhi (IN)

( * ) Notice: Subject to any disclaimer, the term of this patent is extended or adjusted under 35 U.S.C. 154(b) by 762 days.

(21) Appl. No.: 13/981,647

(22) PCT Filed: Feb. 25, 2010

(86) PCT No.: PCT/IN2010/000111
§ 371 (c)(1),
(2), (4) Date: Jul. 25, 2013

(87) PCT Pub. No.: WO2010/097812
PCT Pub. Date: Sep. 2, 2010

(65) Prior Publication Data
US 2013/0331596 A1    Dec. 12, 2013

(30) Foreign Application Priority Data

Feb. 25, 2009  (IN) .............................. 349/DEL/2009

(51) Int. Cl.
*C07C 17/02*   (2006.01)
*C07C 25/02*   (2006.01)
*C07C 253/30*  (2006.01)

(52) U.S. Cl.
CPC .................................. *C07C 253/30* (2013.01)
USPC ........................................... 558/423; 507/206

(58) Field of Classification Search
USPC ........................................... 507/206; 558/423
See application file for complete search history.

(56) References Cited

U.S. PATENT DOCUMENTS

| | | | | |
|---|---|---|---|---|
| 2,095,275 A * | 10/1937 | Wibaut et al. | ................. | 570/206 |
| 2,979,537 A * | 4/1961 | Asadorian | ..................... | 570/206 |
| 3,062,899 A * | 11/1962 | Sax | ................................ | 570/206 |
| 4,831,199 A * | 5/1989 | Suzuki et al. | ................. | 570/208 |
| 4,855,517 A * | 8/1989 | Metz et al. | ..................... | 570/206 |
| 6,740,253 B2 | 5/2004 | Vohra et al. | | |
| 6,956,142 B2 * | 10/2005 | Bedekar et al. | ............... | 570/206 |

FOREIGN PATENT DOCUMENTS

| | | | |
|---|---|---|---|
| FR | 1 375 311 A | | 10/1964 |
| WO | 2004/106227 A1 | | 12/2004 |

* cited by examiner

*Primary Examiner* — Nyeemah A Grazier
(74) *Attorney, Agent, or Firm* — Ladas & Parry LLP

(57) ABSTRACT

A highly pure 3,5-dibromo-4-hydroxybenzonitrile (bromoxynil) has been prepared in high yield from 4-hydroxybenzonitrile using eco-friendly brominating reagent comprising of 2:1 mole ratio of bromide to bromate salts in aqueous acidic medium without any catalyst under ambient conditions with no work up procedure. The product 3,5-dibromo-4-hydroxybenzonitrile was obtained in 91-99% yield with melting point 189-191° C. and more than 99% purity by gas chromatographic analysis without any purification.

6 Claims, No Drawings

PROCESS FOR THE ECO-FRIENDLY PREPARATION OF 3, 5-DIBROMO-4-HYDROXYBENZONITRILE

RELATED APPLICATION INFORMATION

This application is a 371 of International Application PCT/IN2010/000111 filed 25 Feb. 2010 entitled "A Process For The Eco-Friendly Preparation Of 3,5-Dibromo-4-Hydroxybenzonitrile", which was published in the English language on 2 Sep. 2010 with International Publication Number WO 2010/097812 A1 and which claims priority from Indian Patent Application 349/DEL/2009, filed 25 Feb. 2009, the content of which are incorporated herein by reference.

FIELD OF THE INVENTION

The present invention relates to an improved process for the eco-friendly preparation of 3,5-dibromo-4-hydroxybenzonitrile. The present invention particularly relates to a process for the synthesis of 3,5-dibromo-4-hydroxybenzonitrile through in situ generation of hypobromous acid (BrOH).

These bromobenzonitrile derivatives have great economic value since they have been shown to be highly effective when applied to the growth of various crops. These herbicides completely control undesirable vegetation at relatively low application rates without harming the crops and thus allow the crops to grow freely.

BACKGROUND OF THE INVENTION

The use of 3,5-dibromo-4-hydroxybenzonitrile as an herbicide is well established (R. L. Wain Nature, 1963, 200, 28; K. Carpenter and B. J. Heywood Nature, 1963, 200, 28-29). Certain esters of 3,5-dibromo-4-hydroxybenzonitrile, especially the octanoate, have been used extensively as herbicides in the control of broad-leafed weeds, particularly in crop growing areas. Although the esters have thus been shown to be highly effective, they have heretofore been produced only by incurring productivity penalties, which are aggravated by the expensive and cumbersome purifications that have heretofore been required.

Auwers and Reis (1896) in a paper Chem. Ber., 1896, 29, 2355-2360 prepared 3,5-Dibromo-4-hydroxybenzonitrile by a complex four step procedure starting with 4-hydroxybenzaldehyde, an uneconomical procedure involving bromination, formation of the aldoxime, dehydration with concomitant acetate formation and hydrolytic removal of the acetate. The drawback of the process is multi steps are involved to get the final product which makes the process uneconomical.

E. Muller, et al. (1959), [*Chem. Ben* 1959, 92, 2278], has described a procedure for bromination of 4-hydroxybenzonitrile with elemental bromine in methanolic acetic acid. The product produced by the process was recovered by contacting the resulting bromination mixture with aqueous methanolic sodium hydrogen sulfite. The drawback of the process is that elemental bromine is used which is hazardous and difficult to handle.

U.S. Pat. No. 3,349,111 assigned to R. W. Luckenbaugh et al. describes the production of 3,5-dibromo-4-hydroxybenzonitrile or its sodium salt by carrying out bromination with elemental bromine in an aqueous suspension, especially aqueous caustic, followed by a chlorine spurge. The drawback of the process is that elemental bromine is used which is hazardous and difficult to handle. Besides, being an exothermic reaction it is required to cool externally to maintain the desired temperature of the reaction mixture.

U.S. Pat. No. 4,349,488 assigned to D. A Dentel, et al. describes the preparation of 3,5-dibromo-4-hydroxybenzonitrile with liquid bromine using chlorobenzene as solvent under reflux conditions at a temperature about 134° C. The liquid bromine was charged in the reactor for a period for 1 to 1.5 hours. The drawback of the process is that elemental bromine is used which is hazardous and difficult to handle. The temperature was above 130° C. and chlorobenzene was used as solvent is carcinogenic.

U.S. Pat. No. 4,436,665 assigned to R. E Sheds, describes the preparation of 3,5-dibromo-4-hydroxybenzonitrile either with liquid bromine or bromine and chlorine either sequentially or at the same time or with pre-formed bromine chloride or 3% hydrobromic acid. The drawback of the process is the use of elemental bromine which is hazardous and difficult to handle and special equipments are required.

French Pat. No. 1,375,311 describes bromination of hydroxybenzonitrile in acetic acid, obtaining 3,5-dibromo-4-hydroxybenzonitrile in 60% yield. The patent also suggests that by bromination with aqueous sodium hypobromite the product may be obtained in 78% yield. The drawback of the process is that the yield was in the range of 60 to 78% and use of hazardous liquid bromine in acetic acid.

Ramachandraiah et. al, U.S. Pat. No. 6,740,253 describes the process for the preparation of non-hazardous brominating reagents making use of alkaline intermediate from bromine recovery process and alkaline/chlorine at ambient temperature. In this brominating reagent the bromide to bromate ratio was in the range of 2:1 to 2.2:1.0. The limit of the cited patent was only to prepare the brominating reagent and does not to reveal about the preparation of 3,5-dibromo-4-hydroxybenzonitrile.

Ramachandraiah et. al, U.S. patent Ser. No. 10/449,723, describes an improved process of the preparation of brominating reagent by in situ generation of oxidizing agent by purging chlorine to the alkaline bromine solution at ambient temperature. Here also the scope of the invention was limited to the preparation aspects of brominating reagent and does not reveal about the preparation of 3,5-dibromo-4-hydroxybenzonitrile.

Bedekar et. al, U.S. Pat. No. 6,956,142, describes an eco-friendly process for the preparation of bromo benzene using benzene and the brominating reagent at reflux temperature of benzene. Here also the scope of the invention was limited to the preparation of bromobenzene and not mentioned about the preparation of 3,5-dibromo-4-hydroxybenzonitrile.

Varshney, et al. Indian Patent No. 180996 has described an improved process for the synthesis of 3,5-dibromo-4-hydroxybenzonitrile (bromoxynil) from p-cresol comprising (i) brominating p-cresol to make 3,5-dibromo-p-cresol, (ii) oxidizing 3,5-dibromo-p-cresol to 3,5-dibromo-4-hydroxybenzaldehyde; (iii) oximating 3,5-dibromo-4-hydroxybenzaldehyde to 3,5-dibromo-4-hydroxybenzyl oxime and (iv) dehydrating 3,5-dibromo-4-hydroxybenzyl oxime to 3,5-dibromo-4-hydroxybenzonitrile or bromoxynil. The drawback of the invention is that it involves multi steps which make the process cost sensitive and the various steps makes the process complicated.

Vidyasagar, et al. in a paper published in *Indian Journal of Chemistry, Section B*: (1993), 32B, 872 described a two-step synthesis of 3,5-dibromo-4-hydroxybenzonitrile from p-cresol. In the first step p-cresol was brominated with liquid bromine and in the second step it was treated with nitroethane/fused NaOAc in AcOH to give bromoxynil. The drawback of the process is liquid bromine is used as a source of bromine which is hazardous and difficult to handle. Moreover, multi steps are involved and the yield is 87%.

The prior art does not divulge nor teach how 3,5 dibromo-4-hydroxybenzonitrile can be prepared making use of inorganic salts and mineral acid. It is reported for the first time in the present invention how product could be obtained in absence of hazardous liquid bromine, without organic solvent and catalyst at under ambient conditions.

The inventive steps involved in the present invention are i) the soluble brominating reagent with active bromine dispenses the need of hazardous liquid bromine, (ii) the reaction moves forward towards completion without the need of any catalyst, (iii) the process uses only water as dispersing medium and alleviates the need of any solvent and catalyst, v) maximum bromide atom efficiency, and (iv) the reaction is completed at ambient temperature.

OBJECTIVE OF THE INVENTION

The main object of the present invention is to provide an improved process for the eco-friendly preparation of 3,5-dibromo-4-hydroxybenzonitrile (Bromoxynil) which obviates the drawbacks as detailed above.

Another object of the present invention is to dispense the use of liquid bromine in the preparation of 3,5-dibromo-4-hydroxybenzonitrile.

Yet another object of the present invention is to have high atomic substitution of bromine on aromatic substrates in aqueous phase reaction.

Yet another object of the present invention is to use a water soluble and non-hazardous brominating reagent having wide range bromide and bromate ions for bromination process.

Yet another object of the present invention is to carry out the reactions under ambient conditions. Yet another object of the present invention is to obtain high yield and purity of 3,5-dibromo-4-hydroxybenzonitrile.

Yet another object of the present invention is to dispense the use of any catalyst.

Still another object of the present invention is to minimize the workup procedure.

SUMMARY OF THE INVENTION

Accordingly, the present invention provides the eco-friendly synthesis of 3,5-dibromo-4-hydroxybenzonitrile comprising the steps of:
(i) reacting 4-hydroxybenzonitrile in the range of 8.4 to 1260 m moles with a brominating reagent consisting of a alkali/alkaline earth metal bromide and alkali/alkaline earth metal bromate salts wherein the active bromide content in the brominating reagent is 16.8 to 2524 m moles, under continuous stirring;
(ii) adding 0.015 to 3.0 moles of an inorganic acid to the reaction mixture as obtained from step (i) under stirring for a period in the range of 1 to 4 hours at room temperature;
(iii) continuing the stirring further for a period in the range of 1 to 3 hours;
(iv) filtering the solid from liquid, washing with deionized water and drying the precipitate under vacuum at 155-165 mm Hg pressure.

In an embodiment of the present invention, the brominating reagent consist of alkali/alkaline earth metal bromide and alkali/alkaline earth metal bromate salts in the molar ratio of 2:1 to 2.1:1.

In another embodiment of the present invention, the active bromide content in the brominating reagent is at 10% to 20% (w/v) i.e. 16.8 to 2524 m moles.

In another embodiment of the present invention, the bromination reaction is conducted by addition of solid brominating reagent to the aqueous solution containing 4-hydroxy benzonitrile and inorganic acid.

In yet another embodiment of the present invention, inorganic acid used is selected from the group consisting of hydrochloric acid, sulfuric acid, nitric acid, phosphoric acid or perchloric acid.

In still another embodiment of the present invention, the temperature of the reaction is maintained in the range of 25-35° C.

In yet another embodiment of the present invention, water may be used as solvent for the bromination of 4-hydroxybenzonitrile.

In yet another embodiment of the present invention, the yield of the product 3,5-dibromo-4-hydroxybenzonitrile is in the range of 91 to 99%.

DETAILED DESCRIPTION OF THE INVENTION

According to the present invention, 3,5-dibromo-4-hydroxybenzonitrile (bromoxynil) is obtained via the overall reaction depicted in equation 1.

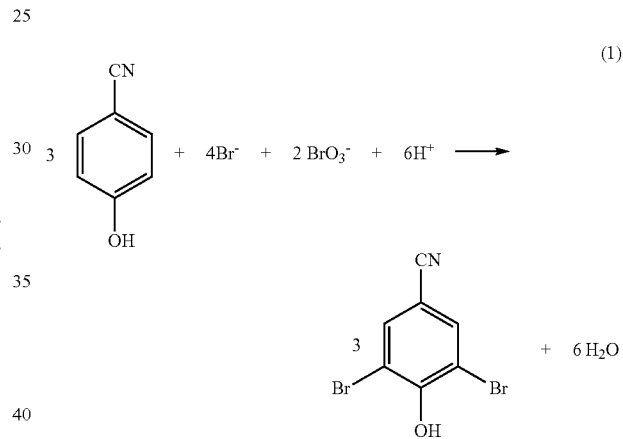

The reaction was carried out in a 10 liter three necked round bottomed flask fitted with the water condenser and addition funnel, mechanical device to stir the contents. Known quantity of 4-hydroxybenzonitrile and required quantity of brominating reagent were taken into a reactor, the contents were stirred to dissolve 4-hydroxybenzonitrile completely. The brominating reagent employed was an intermediate of bromine recovery plant, which comprises of the bromide/bromate in the molar ratio of 2:1, which upon acidification generates reactive species to cause bromination with 100% bromine atom efficiency. A calculated amount of 36% hydrochloric acid was added slowly to the above mixture over a time period of 1-4 hours at room temperature. The stirring was continued further for 1-3 h under the same conditions. The reaction mixture was filtered through Buchner funnel, the solid material was washed once with deionized water, allowed to dry at 80-90° C. and weighed.

The weight of the dried product 3,5-dibromo,4-hydroxybenzonitrile (bromoxynil) was 92-98% yield, purity by GC more than 99%, having melting point 191° C. (Values reported in the literature is 189-191° C.).

In a related procedure, the bromination 4-hydroxybenzonitrile was carried out by taking brominating reagent solution containing required quantities of bromide and bromate salts with slow addition of required quantity of 98% sulfuric acid.

In another related procedure, the required quantity of 36% hydrochloric acid was taken along with the 4-hydroxybenzonitrile dissolved in water and the bromination reaction was carried out by the gradual addition of an aqueous solution containing the required quantities of bromide and bromate salts.

The temperature of the vessel was observed in the range of 25-35° C.

The use of hydrochloric acid is advisable as it generates benign sodium chloride in the effluent reaction minimizes the reaction time.

The reaction product was characterized through elemental analysis, 1H-NMR, IR and melting point.

The purity of the product was checked by gas chromatography.

The said compound in accordance with the invention can be prepared from 4-hydroxybenzonitrile and solid brominating reagent having bromide to bromate ratio of 2:1 at ambient temperature and pressure using water as solvent. The addition of inorganic acid to the reaction mixture assists in-situ generation of hypobromous acid (HOBr) which concomitantly undergo nuclear bromination through substitution on the substrate.

In the present invention, the brominating reagent ($Br^-$/$BrO_3^-$ in 2:1 mole ratio) react with mineral acids and generates the reactive species hypobromous acid (BrOH) equation 2, in solution

$$2Br^- + BrO_3^- + 3H^+ \rightarrow 3BrOH \qquad (2)$$

which reacts with organic substrate 4-cyanophenol without any catalyst in purely aqueous medium to give 3,5-dibromo-4-hydroxybenzonitrile (bromoxynil) in quantitative yield according to the equation 1 above.

The following examples are given by way of illustration of the present invention and therefore should not be construed to limit the scope of the present invention.

Example 1

10 gm of 4-hydroxybenzonitrile (0.084 mol) was taken in a 1 liter two necked round bottomed flask, to it 92 ml of aqueous brominating reagent solution [comprises the bromide and bromate in 2:1 molar ratio with the active (reactive) bromide content 14.57% (w/v)] (0.167 mol) and 310 ml of water was added. The reaction mixture was stirred vigorously to dissolve 4-hydroxybenzonitrile completely. Then 18 ml of 36% HCl (0.18 mol) was added slowly under stirring over a period of 2 h at 28° C. The reaction mixture was allowed to stir for another 2.5 h. The reaction mixture was filtered through Buchner funnel, washed with deionized water, the solid material was allowed to dry at 160 mm Hg pressure and then dried in oven at 80° C. The weight of the dried product was 23.10 gm (99% yield) melting point observed 191° C.

Example 2

1.0 gm of 4-hydroxybenzonitrile (8.40 mmol) dissolved in 40 ml of water was taken in a 100 ml two necked round bottomed flask, to it a solid brominating reagent containing 1.16 g (11.26 mmoles) of sodium bromide and 0.85 g (5.628 mmoles) of sodium bromate was added and stirred for 30 minutes. To the above mixture 1.70 ml of 36% hydrochloric acid (0.017 mol) was added slowly under stirring at 28° C. over a period of 2.0 hours. The reaction mixture was allowed to stir for another 2 to 2.5 h. The reaction mixture was filtered through Buchner funnel, washed with deionized water, the solid material was allowed to dry at 160 mm Hg pressure and then dried in oven at 80° C. The weight of the dried product was 2.210 gm (95% yield) melting point observed 191° C.

Example 3

1.0 gm of 4-hydroxybenzonitrile (8.40 mmol) dissolved in 40 ml of water was taken in a 100 ml two necked round bottomed flask, to it a solid brominating reagent containing 1.16 g (11.26 mmoles) of sodium bromide and 0.85 g (5.628 mmoles) of sodium bromate was added and stirred for 30 minutes. To the above mixture 1.70 ml of 36% hydrochloric acid (0.017 mol) was added slowly under stirring at 32° C. over a period of 2.0 hours. The reaction mixture was allowed to stir for another 2 to 2.5 h. The reaction mixture was filtered through Buchner funnel, washed with deionized water, the solid material was allowed to dry at 160 mm Hg pressure and then dried in oven at 80° C. The weight of the dried product was 2.210 gm (95% yield) melting point observed 191° C.

Example 4

1.0 gm of 4-hydroxybenzonitrile (8.40 mmol) dissolved in 40 ml of water was taken in a 100 ml two necked round bottomed flask, to it 6.7 ml of aqueous brominating reagent solution [comprises the bromide and bromate in 2:1 molar ratio with the active (reactive) bromide content 20% (w/v) 1.153 g (11.19 mmoles) of sodium bromide and 0.85 g (5.60 mmoles) of sodium bromate] was added and stirred for 30 minutes. To the above mixture 1.70 ml of 36% hydrochloric acid (0.017 mol) was added slowly under stirring at 32° C. over a period of 2.0 hours. The reaction mixture was allowed to stir for another 2 to 2.5 h. The reaction mixture was filtered through Buchner funnel, washed with deionized water, the solid material was allowed to dry at 160 mm Hg pressure and then dried in oven at 80° C. The weight of the dried product was 2.265 gm (97% yield) melting point observed 191° C.

Example 5

2.0 gm of 4-hydroxybenzonitrile (16.80 mol) was taken in a 250 ml two necked round bottomed flask, to it 19 ml of aqueous brominating reagent solution [comprises the bromide and bromate in 2:1 molar ratio with the active (reactive) bromide content 14.57% (w/v)] (33.61 mmol) and 60 ml of water was added. The reaction mixture was stirred vigorously to dissolve 4-hydroxybenzonitrile completely. Then 0.91 ml of 98% $H_2SO_4$ (0.0168 mol) was added slowly under stirring over a period of 2.5 h at 28° C. The reaction mixture was allowed to stir for another 2.0 h. The reaction mixture was filtered through Buchner funnel, washed with deionized water, the solid material was allowed to dry at 160 mm Hg pressure and then dried in oven at 80° C., the weight of the dried product was 4.5 gm (97% yield) melting point observed 191° C.

Example 6

150 gm of 4-hydroxybenzonitrile (1.26 mol) was taken in a 10 liter three necked round bottomed flask fitted with the water condenser and addition funnel, to it 1386 ml of aqueous brominating reagent solution [comprises the bromide and bromate in 2:1 molar ratio with the active (reactive) bromide content 14.57% (w/v)] (2.524 mol) and 4.614 lit of water was added (total aqueous medium volume was maintained to 6 lit). The reaction mixture was stirred vigorously for about 1 h to dissolve 4-hydroxybenzonitrile completely. Then 268 ml of 36% HCl (2.61 mol) was added slowly under stirring over a time period of 3.5 h at room temperature. The stirring was continued for another 2.5 hour at 28° C. The reaction mixture was filtered through Buchner funnel, washed with deionized water, the solid material was allowed to dry at 160 mm Hg pressure and then dried in oven at 80° C. The weight of the dried product 3,5-dibromo,4-hydroxybenzonitrile was 343 gm (98% yield), purity by GC more than 99%. melting point observed 191° C.

THE MAIN ADVANTAGES OF THE PRESENT INVENTION

1. The process is easy, eco-friendly and less energetic compared to hitherto known processes.
2. It requires a simple and solid brominating reagent for the in situ generation of reactive species which subsequently is utilized in the bromination of 4-hydroxybenzonitrile.
3. The brominating reagent is solid and non-hazardous and it does not require any special equipment or handling skills.
4. The reaction occurs in solution at the room temperature and atmospheric pressure,
5. The reaction does not require any catalysts.
6. The brominating reagent can easily be obtained at reduced cost from one of the intermediate products in the bromine recovery process.
7. The bromination reaction has high yields and atom efficiency.
8. The product has more than 99% purity.

We claim:
1. A process for the eco-friendly synthesis of 3, 5-dibromo-4-hydroxybenzonitrile comprising the steps of:
  (i) reacting 4-hydroxybenzonitrile in the range of 8.4 to 1260 m moles with a brominating reagent consisting of a alkali/alkaline earth metal bromide and alkali/alkaline earth metal bromate salts wherein the active bromide content in the brominating reagent is 16.8 to 2521 m moles, under continuous stirring;
  (ii) adding 0.015 to 3.0 moles of an inorganic acid to the reaction mixture as obtained from step under stirring for a period in the range of 1 to 4 hours at room temperature;
  (iii) continuing the stirring further for a period in the range of 1 to 3 hours;
  (iv) filtering the solid from liquid, washing with deionized water and drying the precipitate under vacuum at 20.6-21.9 Kilo Pascal pressure.
2. A process as claimed in claim 1, wherein the brominating reagent consist of alkali/alkaline earth metal bromide and alkali/alkaline earth metal bromate salts in the ratio of 2:1 to 2.1:1.
3. A process as claimed in claim 1, wherein the bromination reaction is conducted by addition of solid brominating reagent to the aqueous solution containing 4-hydroxy benzonitrile and inorganic add.
4. A process as claimed in claim 1, wherein inorganic acid used is selected from the group consisting of hydrochloric acid, sulfuric acid, nitric acid, phosphoric acid or perchloric acid.
5. A process as claimed in claim 1, wherein the temperature of the reaction is maintained in the range of 25-35° C.
6. A process as claimed in claim 1, wherein the yield of the product 3,5-dibromo-4-hydroxybenzonitrile is in the range of in the range of 91 to 99%.

* * * * *